United States Patent [19]
Weyl et al.

[11] Patent Number: 6,039,856
[45] Date of Patent: Mar. 21, 2000

[54] MEASURING DEVICE

[75] Inventors: Helmut Weyl, Schwieberdingen; Bernhard Wild, Markgroeningen, both of Germany

[73] Assignee: Robert Bosch GmbH, Stuttgart, Germany

[21] Appl. No.: 09/064,437

[22] Filed: Apr. 22, 1998

[30] Foreign Application Priority Data

Apr. 23, 1997 [DE] Germany ............................ 197 17 036

[51] Int. Cl.⁷ .................................................. G01N 27/28
[52] U.S. Cl. ........................... 204/400; 204/428; 204/431
[58] Field of Search .................................. 204/400, 408, 204/421, 424, 431, 427, 428

[56] References Cited

U.S. PATENT DOCUMENTS

| | | | |
|---|---|---|---|
| 4,609,454 | 9/1986 | Ziegler ..................................... | 204/408 |
| 4,668,477 | 5/1987 | Nishio et al. ............................ | 204/428 |
| 4,948,491 | 8/1990 | Kato et al. ............................... | 204/424 |
| 5,246,562 | 9/1993 | Weyl et al. .............................. | 204/428 |
| 5,403,464 | 4/1995 | Mayer et al. ............................ | 204/431 |
| 5,679,226 | 10/1997 | Furusaki et al. ........................ | 204/424 |
| 5,698,084 | 12/1997 | Weyl et al. .............................. | 204/424 |
| 5,804,050 | 9/1998 | Hayakawa et al. ..................... | 204/408 |
| 5,900,129 | 5/1999 | Tsuji et al. .............................. | 204/424 |

FOREIGN PATENT DOCUMENTS

| | | |
|---|---|---|
| 56-133653 | 10/1981 | Japan . |
| 2-238355 | 9/1990 | Japan . |

*Primary Examiner*—Elizabeth McKane
*Assistant Examiner*—Andrew Aldag
*Attorney, Agent, or Firm*—Kenyon & Kenyon

[57] ABSTRACT

A measuring device, in particular, an electrochemical sensor, has a sensor element arranged at a measuring point. The sensor element is arranged in a housing and is connected via electrical connecting lines to an evaluation circuit away from the measuring point. The electrical connecting lines are run, at least in the vicinity of the measuring point, in a protective device. The protective device forms a sealing seat with the housing. The housing in the area of the sealing seat, at least in some areas, has a coating.

14 Claims, 2 Drawing Sheets

MEASURING DEVICE

FIELD OF THE INVENTION

The present invention relates to a measuring device, in particular, an electrochemical sensor (detecting element).

BACKGROUND INFORMATION

Measuring devices are known. For example, electrochemical sensors, formed in a so-called finger type of construction, are installed in motor vehicles for determining the oxygen content in the exhaust gases of internal combustion engines. These measuring devices possess one sensor element which is arranged directly at a measuring point and which is tightly secured in a housing.

The sensor element, as is known, has a solid electrolyte arranged between two electrodes. According to the makeup of the sensor element, an additional heating element is provided. To evaluate the sensor signals detected by the sensor element, or to supply the sensor element with the necessary heating voltage, provision is made for electrical connecting lines, which connect the sensor element to a corresponding circuit arrangement.

Since the sensor element, for example in measuring the oxygen content in exhaust gases, is arranged in an area which is acted upon by a relatively high temperature and in which an increased danger of contamination exists, it is known to shield the electrical connecting lines at least in the vicinity of the measuring device. For this purpose, it is known to run the electrical connecting lines in a protective device designated as a hollow lead. This hollow lead, which is also made of an elastic hose, engages with a shoulder (collar) of the measuring device housing and forms a sealing seat with the latter. In this connection, a form-locking fit obtains between the protective device and the housing. The known sealing seat has the disadvantage that although sufficient protection is afforded against coarse contamination, e.g., from spray water, nevertheless, fine contamination, such as is caused by a mist-like condensation, as occurs precisely in the mounting location of measuring devices in motor vehicles, is not countered by an adequate sealing effectiveness.

The mist-like condensation spreads along the sealing surfaces of the protective device and the housing, which form the sealing seat, and in this way penetrates into the interior of the measuring device.

SUMMARY OF THE INVENTION

The measuring device of the present invention has the advantage that it is simple to construct and offers a high level of sealing protection. An absolute sealing tightness of the sealing seat is obtained by the housing having a coating, at least in some areas, in the area of the sealing seat, the coating creating a form- and force-locking fit between the housing and the protective device. As a result of the form and force-locking fit between the protective device and the housing, a barrier is established against contact with even mist-like contaminants, so that the spreading contaminants are prevented from passing through the sealing seat.

In a preferred embodiment of the present invention, provision is made that the coating be a PTFE (polytetrafluoroethylene) coating. In this way, a force-locking fit is achieved between the PTFE coating of the housing and the protective device, which is preferably made of a PTFE material, as a result of the hydrophobic properties of the PTFE material. As a result of the water-repelling effect associated therewith, moisture is prevented from penetrating through the sealing seat into the housing.

Due to its high temperature resistance, the PTFE material is additionally suitable for ensuring a permanent sealing effectiveness for the measuring device even under temperature stressing of the housing.

In a further preferred embodiment of the present invention, provision is made that the coating be a PFA (polyfluoroamide) coating. In this way, the property of the material, namely to develop an adhesive effect starting at a certain temperature, is exploited, in that the sealing seat is heated to this required temperature. As a result of the heating, the PFA coating liquefies and produces a form- and force-locking sealing seat between the protective device and the housing. Provision is preferably made to liquefy the PFA coating only partly, through a controlled heating, in particular by an inductive heating, so that the PFA coating remains stable in form and permits a defined production of the sealing seat. In this way, under the given use conditions of the measuring device, a permanent sealing-off of the interior space of the measuring device is assured in a simple manner at the sealing seat between the protective device and the housing.

DETAILED DESCRIPTION

Figure 1:
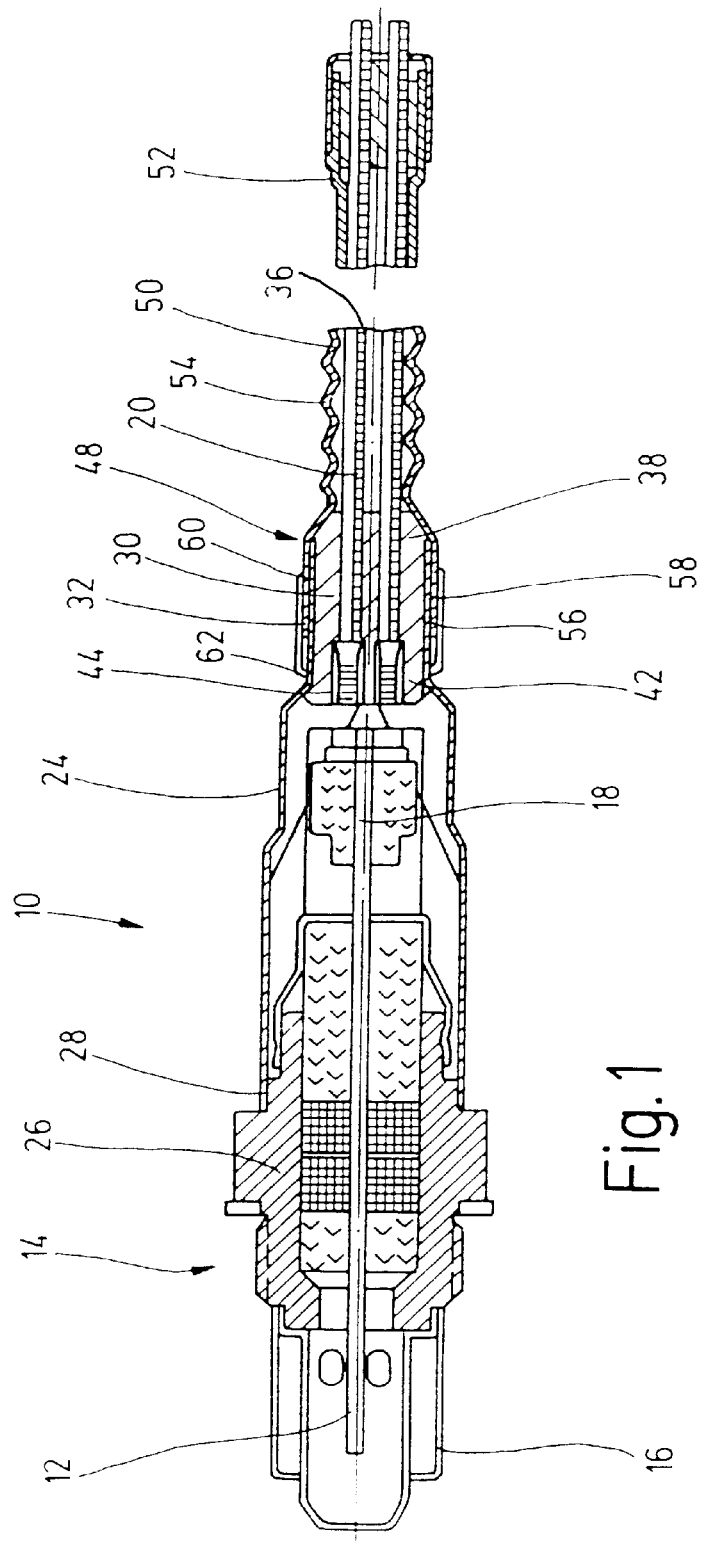
FIG. 1 shows a schematic longitudinal section of a measuring device.

FIG. 1 shows a measuring device 10 in a longitudinal section. The design and the function of measuring device 10 are generally known.

Measuring device 10 has a sensor element 12. Sensor element 12 can, in principle, be any sensor element for measuring a physical quantity. In the example depicted, it is assumed that sensor element 12 is an electrochemical sensor 14, which is used to determine the oxygen content in the exhaust gases of internal combustion engines. Sensor element 12 is arranged in housing 16, which can be secured in an undepicted exhaust pipe. Housing 16 is conveyed through a through hole of the exhaust pipe and is secured by appropriate fastening means, for example, a union nut. Housing 16 is mounted by being sealingly arranged in the through hole.

Housing 16 contains electrodes, which are not depicted here in detail, as well as a heating device 18, by means of which, in a manner not to be elaborated on further here, the oxygen concentration in the exhaust gas of an internal combustion engine can be measured. The electrodes and heating device 18 are connected, via electrical connecting lines 20, to a corresponding evaluation or control circuit.

Connecting lines 20, on the one hand, function to tap off sensor signals and, on the other hand, to make a heating voltage available.

Figure 2:
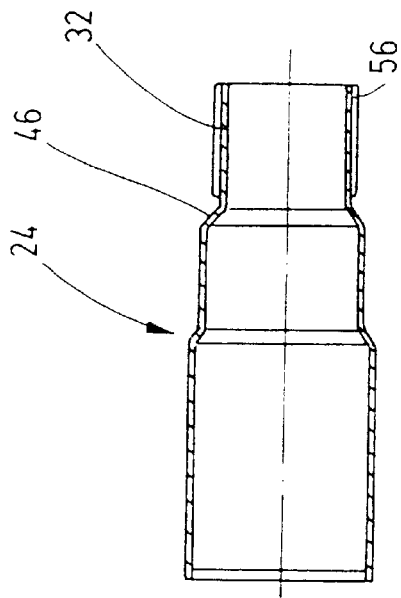
FIG. 2 shows a longitudinal section of a housing part of the measuring device.

At its end away from the measuring point, housing 16 gradually passes over into a protective sleeve 24. Protective sleeve 24 can be formed either in one piece with housing 16, or, as in the depicted example, as a separate part, which is fixedly connected to measuring sensor 14. For this purpose, measuring sensor 14 has a ceramic substructure 26, which has a correspondingly formed shoulder 28. As FIG. 2 shows in more detail, protective sleeve 24 is configured as a rotationally symmetrical stepped part, i.e., the diameter of protective sleeve 24 decreases by steps over its axial extension. In this way, on the one hand, the mechanical stability of protective sleeve 24 is enhanced and, on the other hand, an input diameter on the side of shoulder 28 can be adjusted to an output diameter, depicted at the right in FIG. 2, leading to a protective device which has yet to be explained.

Protective sleeve 24 has a support sleeve 30, which is arranged within segment 32, which has the smallest diameter of the steps of the protective sleeve. Support sleeve 30 is made of a flexible material and has through holes 36 running in the axial direction which function to accommodate connecting lines 20. The number of connecting lines 20 corresponds to the number of through holes 36. The axial extension of support sleeve 30 is greater than the axial extension of segment 32 of protective sleeve 24, so that support sleeve 30 at one end 38 extends beyond protective sleeve 24. The external diameter of support sleeve 30 is selected so that it can be pressed into segment 32 of protective sleeve 24 without play, and can be fixed because of its elasticity. In this connection, support sleeve 30 is compressed so that, at its end 42 arranged within protective sleeve 24, a shoulder 44 is produced, which grips a, for example, conical transitional area 46 of protective sleeve 24 from behind, leading to a segment having a greater diameter. In this way, it is possible to insert support sleeve 30 tightly into protective sleeve 24. Support sleeve 30 is preferably made of a PTFE material. Through holes 36 are preferably constituted such that connecting lines 20 are also sealingly led through them, i.e., no leaks exist between the external casing of connecting lines 20 and through-holes 36. At the same time, support sleeve 30 provides strain relief for connecting lines 20.

End 38 of support sleeve 30 is arranged within a mounting segment 48 of an elastic hollow element 50. Hollow element 50 is designed as a molded hose, the latter having at its one end mounting segment 48, at its other end a mounting segment 52, and between mounting segments 48 and 52 a support segment 54. Mounting segment 48 has an inner diameter which permits it to slide onto segment 32 of protective sleeve 24. In this connection, the axial length of mounting segment 48 is selected such that when mounting segment 48 has been slid onto segment 32, it overlaps entire segment 32 and contacts end 38 of support sleeve 30, which extends beyond segment 32.

As is clear from FIG. 2, segment 32 of protective sleeve 24 has a coating 56 on its outer periphery. Coating 56, according to a first exemplary embodiment, is made of a PTFE material, which is applied to segment 32 using an appropriate method. For this purpose, special coating techniques are known which permit metals to bond, here protective sleeve 24 and PTFE material. Coating 56 is applied at relatively low strength, so that it is possible to slide fastening end 48 onto segment 32 having its coating 56.

As a result of providing for coating 56 of a PTFE material in the area of hollow element 50, which is slid onto protective sleeve 24, a sealing seat 60 is formed between coating 56, which is permanently bonded to protective sleeve 24, and mounting segment 48 of hollow element 50. The sealing surfaces are constituted, on the one hand, by the outer surface of coating 56 and, on the other hand, by the inner surface of mounting segment 48. In this way, a relatively large sealing surface is achieved, which prevents contamination from penetrating into protective sleeve 24 and thus into housing 16. Since both coating 56 and hollow element 50 are made of a PTFE material, sealing seat 60 is formed out of two sealing surfaces of PTFE material, which are situated directly opposite each other. PTFE material is known to have distinctly hydrophobic properties, i.e., mutually facing boundary layers of PTFE material achieve a force-locking fit. At the same time, a water-repellant effect is thus achieved, so that even mist-like contaminants, or moisture, are not able to pass through sealing seat 60.

Sealing seat 60 is secured by a sleeve 58, which surrounds sealing segment 48. Sleeve 58 has a neck-shaped shoulder 62, molded to the inside, which functions, on the one hand, as supporting element for segment 32 of protective sleeve 24, and, on the other hand, as a limit stop for mounting segment 48. Sleeve 58 is plastically deformed by the application of an external mechanical force, at least in areas, a so-called caulking, so that mounting segment 48 is fixedly squeezed between sleeve 58 and segment 32. Overall, the result is thus a mechanically more secure connection, i.e., one capable of sustaining strain between pipe element 50 and protective sleeve 24, or housing 16, the connection also having, in addition, great sealing effectiveness, as was already explained, due to the formation of sealing seat 60.

According to a further exemplary embodiment, coating 56 can also be made of a PFA material. It is known that PFA materials begin to liquefy when heated to a certain temperature, approximately from 310 to 330° C. In this temperature range, a certain viscosity of the PFA material is achieved, so that it develops an adhesive effect. These known properties of PFA material are exploited by heating sealing seat 60 to a defined temperature, after sliding mounting segment 48 onto protective sleeve 24 having coating 56.

Figure 3:
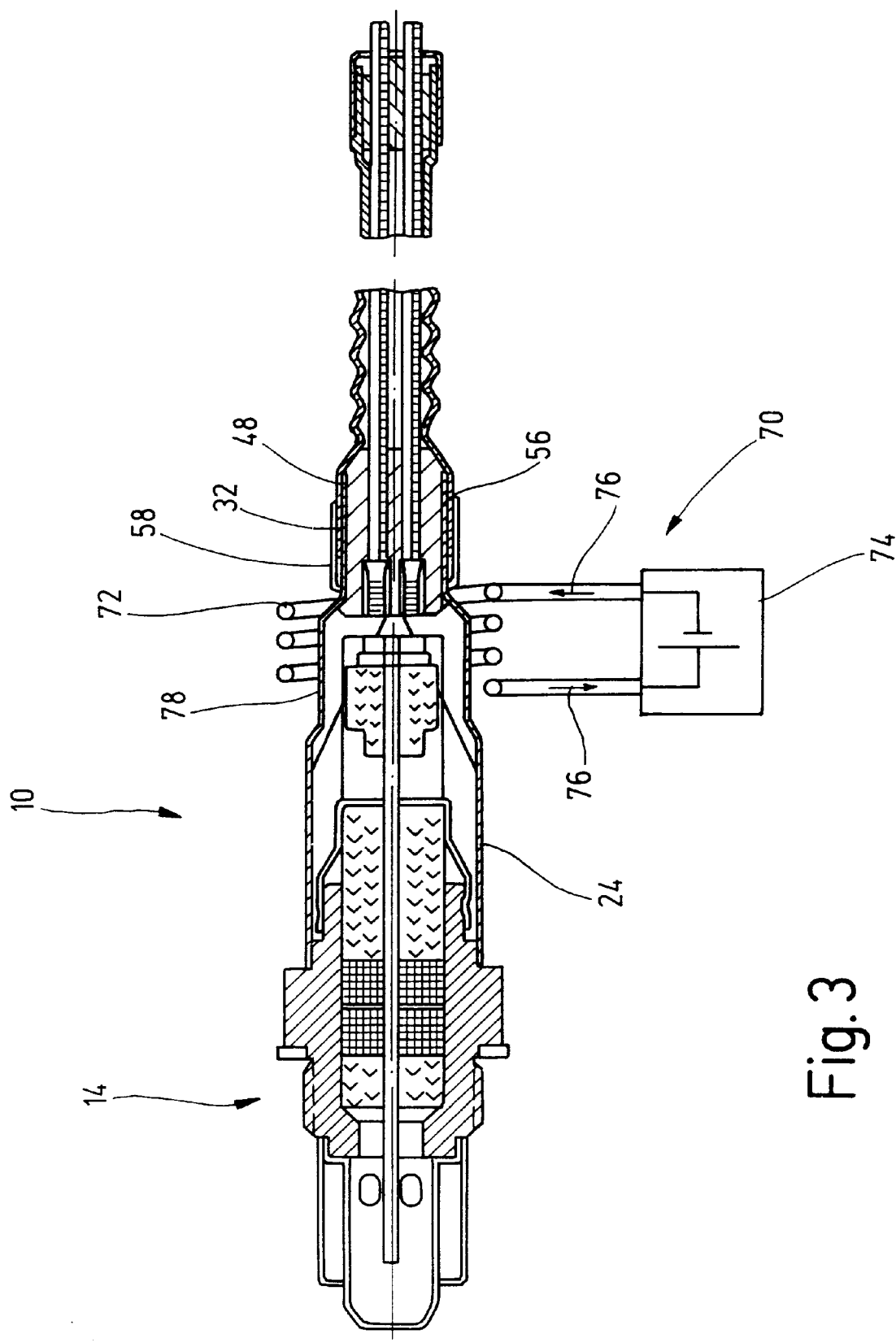
FIG. 3 shows schematically the production of a sealing seat according to the present invention.

For this purpose, the device indicated schematically in FIG. 3 can be used. FIG. 3 shows, on the one hand, the longitudinal section of measuring device 10 according to FIG. 1, so that generally the description in that regard is applicable here.

For manufacturing a form-and force-locking sealing seat 60 between mounting segment 48 and coating 56, and thus protective sleeve 24, provision is made for a device, designated throughout as 70. Device 70 possesses an induction coil 72, whose inner diameter is selected such that measuring instrument 10, at least with respect to segment 32 of protective sleeve 24, can be inserted into it. Induction coil 72 is connected to a voltage source, for example, a high frequency generator 74. Moreover, the coil lines of induction coil 72 can be designed so that a circulation circuit 76 of a coolant, for example, air or water, can be maintained. The manner of functioning of a such a device 70 operating on the basis of an induction coil 72, is well known. By switching on high frequency generator 74, heat energy is produced by induction coil 72, the heat energy making it possible to apply this heat energy in a defined manner to measuring device 10. Since protective sleeve 24 is made of a metallic material, it is suitable as a heat conductor. By heating protective sleeve 24 at its segment 78, heat is conducted, inter alia, in the direction of segment 32, so that coating 56 made of PFA material applied to segment 32 is also heated. Through the defined heating, which can be adjusted, for example, regarding a period of heating, a level of current flow through induction coil 72, or other suitable precautions, coating 56 is heated to a defined degree so that it becomes viscous.

As a result of the subsequent caulking of sleeve 58, mounting segment 48 is pressed against coating 56, which has melted from the effect of the heat, so that, after the cooling and resolidifying of coating 56, an interior form and force locking bond results between mounting segment 48 and coating 56. In this way, sealing seat 60 is formed having permanent, powerful sealing effectiveness.

Whether coating 56 is manufactured out of a PTFE material or a PFA material, it is assured that, due to operating temperatures of, for example, about 250 to 300° C., which arise during the normal use of measuring device 10, a temperature resistance of sealing seat 60 is produced such that measuring device 10 is permanently sealed off against penetration of external contaminants.

What is claimed is:

1. A measuring device comprising:

a housing, the housing being a protective sleeve;

a sensor element arranged in the housing at a measuring point, the sensor element being connected via electrical connecting lines to an evaluation circuit spaced from the measuring points;

a second sleeve arranged within a section of the protective sleeve, the second sleeve having feed-through openings which receive the electrical connecting lines; and a protective device through which the electrical connecting lines extend to the protective sleeve, the protective device protecting the electrical connecting lines, the protective device including a connecting section which extends over the section of the protective sleeve, the protective sleeve having a coating formed thereon at least in an area of the connecting section, the coating not contacting the second sleeve, the coating forming a sealing seat between the protective sleeve and the protective device.

2. The measuring device according to claim 1, wherein the sensor element is an electrochemical sensor.

3. The measuring device according to claim 1, wherein the coating is a PTFE coating.

4. The measuring device according to claim 1, wherein the coating is a polyflouramide coating.

5. The measuring device according to claim 1, wherein the coating is heated above a melting point of the coating and is deformed by a mechanical force during or after the heating, to provide a form-locking and force-locking fit.

6. The measuring device according to claim 5, wherein the heating proceeds inductively.

7. The measuring device according to claim 1, wherein the protective device is made of a PTFE material.

8. A measuring device comprising:

a housing, the housing being a protective sleeve;

a sensor element arranged in the housing at a measuring point, the sensor element being connected via electrical connecting lines to an evaluation circuit spaced from the measuring point;

a second sleeve arranged within a section of the protective sleeve, the second sleeve having feed-through openings which receive the electrical connecting lines;

a protective device through which the electrical connecting lines extend to the protective sleeve, the protective device protecting the electrical connecting lines, the protective device including a connecting section which extends over the section of the protective sleeve, the protective sleeve having a coating formed thereon at least in an area of the connecting section, the coating forming a sealing seat between the protective sleeve and the protective device; and a further sleeve surrounding the connecting section.

9. The measuring device according to claim 8, wherein the sensor element is an electrochemical sensor.

10. The measuring device according to claim 8, wherein the coating is a PTFE coating.

11. The measuring device according to claim 8, wherein the coating is a polyflouramide coating.

12. The measuring device according to claim 8, wherein the coating is heated above a melting point of the coating and is deformed by a mechanical force during or after the heating, to provide a form-locking and force-locking fit.

13. The measuring device according to claim 12, wherein the heating proceeds inductively.

14. The measuring device according to claim 8, wherein the protective device is made of a PTFE material.

\* \* \* \* \*